United States Patent [19]

Schmalfuss et al.

[11] Patent Number: 4,815,844
[45] Date of Patent: Mar. 28, 1989

[54] DEVICE FOR TESTING COMPONENTS OF TRANSPARENT MATERIAL FOR SURFACE IRREGULARITIES AND OCCLUSIONS

[75] Inventors: Harald Schmalfuss, Rodgau; Friedel Sinsel, Frankfurt am Main; Reinhold Bolz, Floersheim, all of Fed. Rep. of Germany

[73] Assignee: Battelle-Institut e.V., Frankfurt am Main, Fed. Rep. of Germany

[21] Appl. No.: 62,183

[22] Filed: Jun. 15, 1987

[30] Foreign Application Priority Data

Jun. 14, 1986 [DE] Fed. Rep. of Germany ....... 3620129

[51] Int. Cl.⁴ ............................................. G01N 21/88
[52] U.S. Cl. .................................... 356/237; 356/124; 356/239; 356/426; 250/572
[58] Field of Search ............... 356/124, 237, 239, 426; 250/563, 572

[56] References Cited

U.S. PATENT DOCUMENTS

| | | | |
|---|---|---|---|
| 3,892,494 | 7/1975 | Baker et al. | 356/237 |
| 3,947,127 | 3/1976 | Bennett et al. | 356/124 |
| 3,988,068 | 10/1976 | Sprague | 356/124 |
| 4,460,273 | 7/1984 | Koizumi et al. | 356/239 |

FOREIGN PATENT DOCUMENTS

| | | |
|---|---|---|
| 2337597 | 2/1974 | Fed. Rep. of Germany . |
| 3011014 | 10/1980 | Fed. Rep. of Germany . |
| 3237511 | 4/1984 | Fed. Rep. of Germany . |
| 1242780 | 7/1986 | U.S.S.R. ............... 356/237 |

Primary Examiner—F. L. Evans
Attorney, Agent, or Firm—Spencer & Frank

[57] ABSTRACT

A device for testing components of transparent material for surface irregularities and occlusions which comprises a mechanism for rotatably mounting the component so that the component may be rotated on its axis; a mechanism for generating a light ray which moves linearly so that the light ray can dot-scan the component along a diameter of the component; at least one signal generating device disposed at a predetermined angle to the direction of impingement of the light ray for detecting surface irregularities and occlusions of the component and then generating a signal representative of the irregularity or occlusion; and a signal evaluation device for evaluating the signals produced in the signal generating device. The signal generating device comprises an image forming optical system; an interchangeable mask disposed at the focal plane of the image forming optical system for selecting the image of a plane of the component; and a receiver for receiving the light rays passing the mask and generating a signal representative of the light rays received.

7 Claims, 4 Drawing Sheets

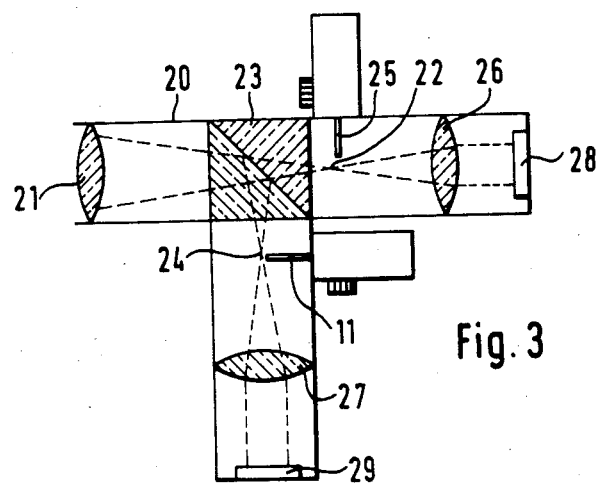
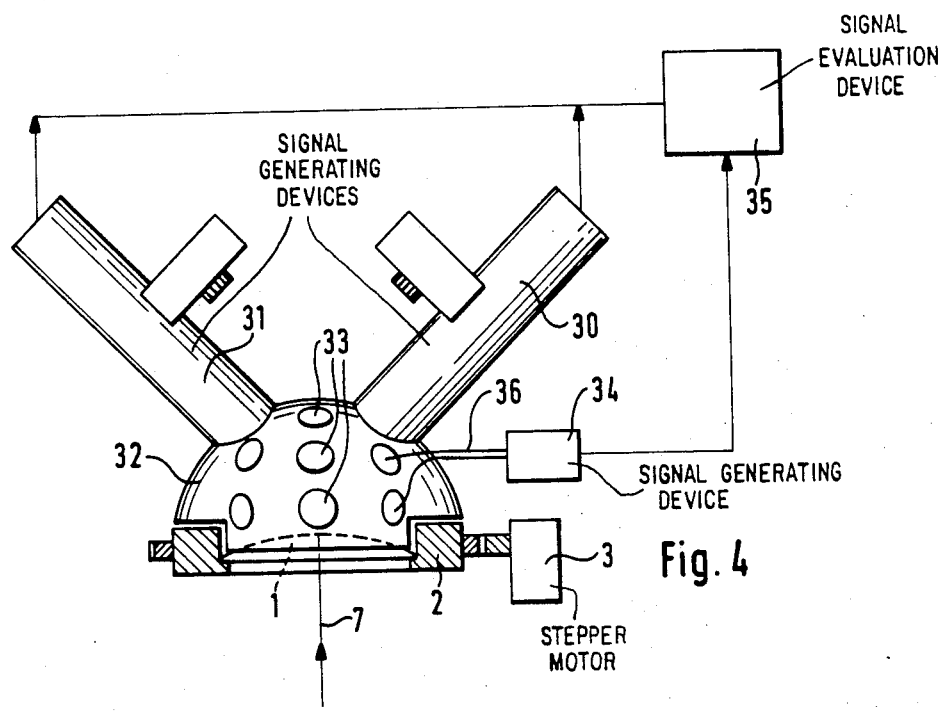

DEVICE FOR TESTING COMPONENTS OF TRANSPARENT MATERIAL FOR SURFACE IRREGULARITIES AND OCCLUSIONS

BACKGROUND OF THE INVENTION

1. Field of the Invention

The invention in question concerns a device for testing components of transparent material for surface irregularities and occlusions by dot-scanning the component by a light ray and detecting the light which is diffracted by the surface irregularities or occlusions.

Components of transparent material, for example optical or ophthalmic lenses, must be tested for flaws prior to their utilization, particularly for surface flaws such as scratches, smears, cracks, chipping, stains, and for occlusions such as bubbles or streaks. Such flaws would limit the usability of a lens if these were to exceed the limit values stated in DIN 3140.

2. Discussion of the Prior Art

Conventionally, the testing of optical components is carried out by personnel in the form of visual inspection. Such a test must be performed, to a large extent, in a darkened room. It is expensive, not sufficiently objective and, due to the high degree of monotony of the testing procedure, not sufficiently reliable.

Efforts have, therefore, been made to develop methods and devices for automatic, objective testing of optical components.

From DE-OS No. 32 37 511, the method of placing optical components to be tested in the optical beam path of a television camera and of displaying through the component, a test pattern on the camera is known. The disturbances caused by flaws in the component, produce a video signal which deviates from the control signal not influenced by the component. The flaw is deduced on the basis of the deviation between the control and actual signal. A device acting on this principle is rather expensive and is not able to detect smaller flaws, for example, those resulting from scratches, smears or hairline cracks.

In order to increase the sensitivity of the testing procedure, it is recommended in DE-OS No. 30 11 014 that the component to be tested be illuminated completely, a television image be produced, and the video signal be analyzed line for line. This method is also not sufficiently exact.

An even older recommendation for a test method is to be found in DE-OS No. 23 37 597. According to this disclosure, a light ray is focused on the surface of the component to be tested and is punctiformly moved over the surface, at the same time being kept in focus. The light penetrating the component is reflected backwards, passes through the component again, and then falls onto a detector. Deviations in the intensity of the receiver signal make it possible to deduce a flaw and also to localize this flaw.

A device acting on this principle is very expensive. It only allows that surface of the work-piece to be tested onto which the scanner ray is focused.

SUMMARY OF THE INVENTION

It is the object of the present invention to create a device for testing components of transparent material for surface irregularities and occlusions, which makes possible reliable detection of such irregularities in one or more preselected planes or surfaces of the component.

This device for testing components of transparent material for surface irregularities and occlusions comprises a mechanism for rotatably mounting the component so that the component may be rotated on its axis; a mechanism for generating a light ray which moves linearly so that the light ray can dot-scan the component along a diameter of the component; at least one signal generating device disposed at a predetermined angle to the direction of impingement of the light ray for detecting surface irregularities and occlusions of the component and then generating a signal representative of the irregularity or occlusion; and a signal evaluation device for evaluating the signals produced in the signal generating device. The signal generating device comprises an image forming optical system; an interchangeable mask disposed at the focal plane of the image forming optical system for selecting the image of a plane of the component; and a receiver for receiving the light rays passing the mask and generating a signal representative of the light rays received.

With the device in accordance with the invention, by means of the scanning light beam, a light section is produced through the component to be tested. This light section is displayed via the signal generating device, whereby only the light diffracted by flaws in the component is used to produce the image. The angle formed by the optical axis of this device and the rotating axis of the component, is advantageously adjustable. It can, depending on the deflection behaviour of the flaw to be determined, be between 10° and 60°, an angle of 40° having proven to be expedient. This allows scratches, hairline cracks and other, relatively sharply defined flaws in the surface of the component to be detected.

With the device in accordance with the invention, the mask provided in the image plane of the signal generating device separates the images of the back and front of the component to be tested. If the masks are designed accordingly, an inner plane of the component can be used for flaw detection.

The configuration for evaluation of the image signals generated can, for instance, be designed as a monitor on which virtually a dark-field image of the lens surface to be scanned appears, in which the flaws are brightly displayed.

An automatic configuration can also be provided, which detects the flaws in accordance with specific criteria and classifies these according to size, frequency and location in conformity with DIN No. 3140, Parts 2 and 7. Such a configuration is, for example, the subject of Patent Application No. P3620146.4 with the title "Method for Testing Components of Transparent Material for Surface Irregularities and Occlusions", which was submitted by the Applicant on June 14th, 1986, which application corresponds to U.S. application Ser. No. 062,181 filed June 15th, 1987. An automatic device such as this allows series-testing of optical components.

A further development of the device in accordance with the invention, enables the front and back of the component to be tested separately or simultaneously.

It has proven advantageous to design the device so that two signal generating devices art provided and symmetrically disposed to the rotational axis of the component.

Flaws in the component which are not sharply defined do not diffuse the impinging light isotropicly, but highly anisotropicly at a narrowly defined dihedral angle which can assume very high values. Such non-sharply defined surface flaws are, for instance, smears. These flaws can generally not be detected with the device described in the aforegoing. It is, therefore, of particular advantage to design the device so that it incorporates a hemispherical shell above the component and an additional light detecting means arranged to provide additional system generation.

BRIEF DESCRIPTION OF THE DRAWINGS

On the basis of FIGS. 1 to 5 of the enclosed drawings, the invention will be more closely explained in the following. In detail:

FIG. 3 shows a further embodiment of a single generating device for generating signals;

FIG. 4 shows a further embodiment of the device in accordance with the invention;

DESCRIPTION OF THE PREFERRED EMBODIMENT

Figure 1:
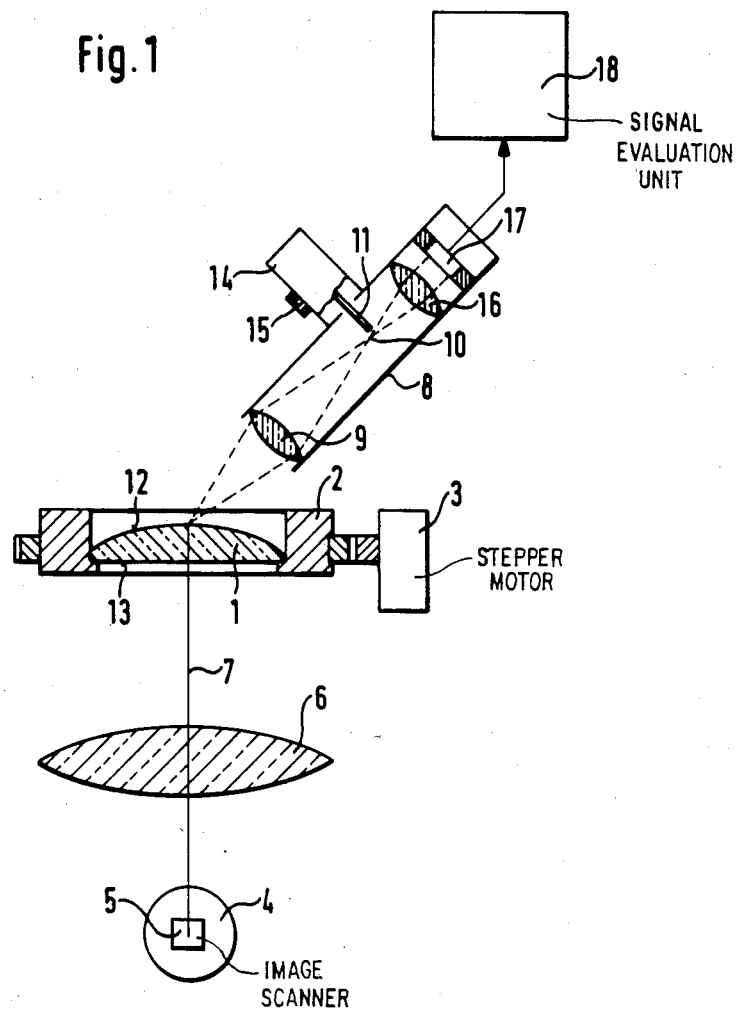
FIG. 1 shows, in the form of a basic drawing, a one embodiment of the device in accordance with the invention.

In FIG. 1, a lens (1) of transparent material is to be examined for surface flaws. This lens (1) is placed on a rotary plate (2), which is turned by means of the stepper motor (3).

A laser (4), whose parallel light beam (7) is linearly deflected within a preset dihedral angle by means of an image scanner (5), illuminates the lens (1). A focusing lens (6) is arranged in such a way that one of its focal points coincides with an edge of the image scanner (5). As a result, the deflected light beams are moved in parallel behind the lens (6), namely, along a diameter of the lens (1) between the extreme positions (7a) and (7b). Such an illumination system is the subject of the Patent Application No. P3620108.1 with the title "Device for Illuminating Components of Transparent Material in Testing for Irregularities", which was submitted by the Applicant on June 14th, 1986, which application corresponds to U.S. application Ser. No. 062,182 filed June 15th, 1987.

The resulting light section of the laser beam (7) and the lens (1), is scanned by means of a signal generating device (8), which is arranged inclined towards the rotational axis of the lens (1). The angle of inclination of the signal generating device (8) is selected in such a way that it catches the isotropicly diffused light from the surface flaws of the lens (1) and, via the image-forming optical system (9), which, for example, is constructed as a zoom lens in the intermediate image plane (10), displays this. In the intermediate image plane (10), a mask (11) is arranged, which masks either the image of the front surface (12) or the image of the back surface (13) of the lens (1). The mask (11) is arranged on a rotary plate in the housing (14). Via a push-button (15), the mask (11) required in each case can be swung into the beam path.

The light passing the mask (11) is projected via a relay lens (16) onto a detector (17) in such a way as to fill the screen. The image signals produced by this are transferred to a diagrammatically illustrated signal evaluation unit (18).

In the case of biconcave, biconvex, plano-concave and plano-convex lenses (1), the mask (11) consists of only a single straight cutter. For concave-convex lenses, in addition to a cutter mask, curved masks are also necessary in order to be able to clearly separate both lens surfaces.

By designing the mask (11) appropriately, it is also possible to select a plane between the surfaces (12) and (13) of the lens (1) for signal acquisition. This plane allows examination for occlusions.

The detector (17) can also be designed as a line detector with high-sensitive resolution. In this case, the mask (11) must be movable, in order to be able to separate the lens surfaces for evaluation via software in the signal evaluation unit (18).

Instead of solid masks (11), it is also possible to use a mask, the optical transparency of which is controllable.

Figure 2:
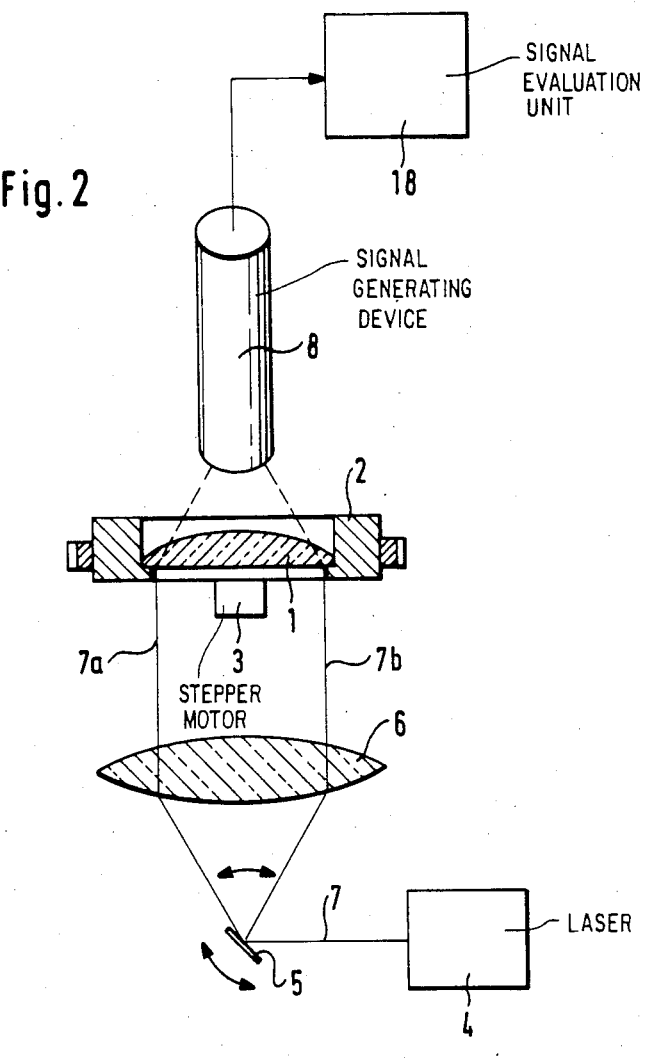
FIG. 2 shows the embodiment of FIG. 1 turned by 90°.

Instead of the signal generating device (8) for signal acquisition as depicted and described in connection with FIGS. 1 and 2, a signal generating device can also be employed such as is illustrated, for example, in FIG. 3. This signal generating device (20) consists of a lens (21) which projects the light section through the lens (1) to be tested into the intermediate image plane (22). A divider cube (23) is arranged between the lens (21) and the intermediate image plane (22), which deflects a portion of the light by 90°. This deflected light is reproduced in the second intermediate image plane (24). An interchangeable mask (25) is arranged in the intermediate image plane (22) which, for instance, masks out the image of the front surface (12) of the lens (1). A mask (11) is also arranged in the intermediate image plane (24) of the lateral branch of the signal generating device (20), which, for instance, masks out the image of the back surface (13) of the lens (1). The light passing the masks (22) and (24) is, via relay lenses (26) and (27), reproduced on diagrammatically illustrated detectors (28) and (29).

The signal generating device (20) can, by providing a further divider cube, also be designed in such a way that simultaneous reception of three evaluation signals from three different surfaces or planes of the lens (1) is possible.

In the case of the variant of the new device illustrated in FIG. 4, two signal generating devices (30) and (31) are provided for signal acquisition, which are arranged symmetrical to the rotational axis of the lens (1). Signal generating devices (30) and (31) can both, for example, be designed as per FIG. 3. With these devices, it is possible to detect those surface flaws in the back or front of the lens (1) which are relatively sharply defined and which isotropicly diffuse the light. Such flaws are, for instance, scratches and hair-line cracks. Problems have been experienced with surface flaws which only cause slight indentation of the surface. These flaws are known as smears. It has been found that smears diffuse the light in a strongly anisotropic manner, namely, only within a narrowly defined dihedral angle which can assume high values. In order to also be able to detect these surface flaws, a so-called integral lens is provided in the form of a hemisphere (32). A number of holes (33) which, in each case, accommodate a small image lens and a post-installed detector, are distributed over this hemisphere (32). An adjustable preamplifier is allocated to each detector, and the signals of all detectors are fed to a signal combination stage (34) which forms these into one signal, comparable in its strength to the signals supplied by the signal generating devices (30) and (31).

All signals, i.e. the signals from the signal generating devices (30) and (31) as well as the signals from the signal combination stage (34), are passed together to a signal evaluation device (35) for electronic signal evaluation.

It is also possible to install in the holes (33) of the hemisphere (32) only one image lens in each case, which guides the impinging light to an incoherent light beam (36). All these light beams lead together to a detector which is provided instead of the signal combination stage (34) of FIG. 4.

The signal generating devices (30) and (31) can differentiate between the signals assigned to the front or back of the lens (1). This cannot be done by the integral lens of the hemisphere (32). It is, therefore, necessary to provide a means in the signal evaluation device (35) of linking all signals led in. Since, by means of the dot-type scanning, it is possible at any time to scan the output signals of the receiver for coincidental events, the information packed in the integral receiver can be assigned to the individual lens sides, provided that at least some image dots are also recognized by the signal generating devices (30) and (31).

Figure 5:
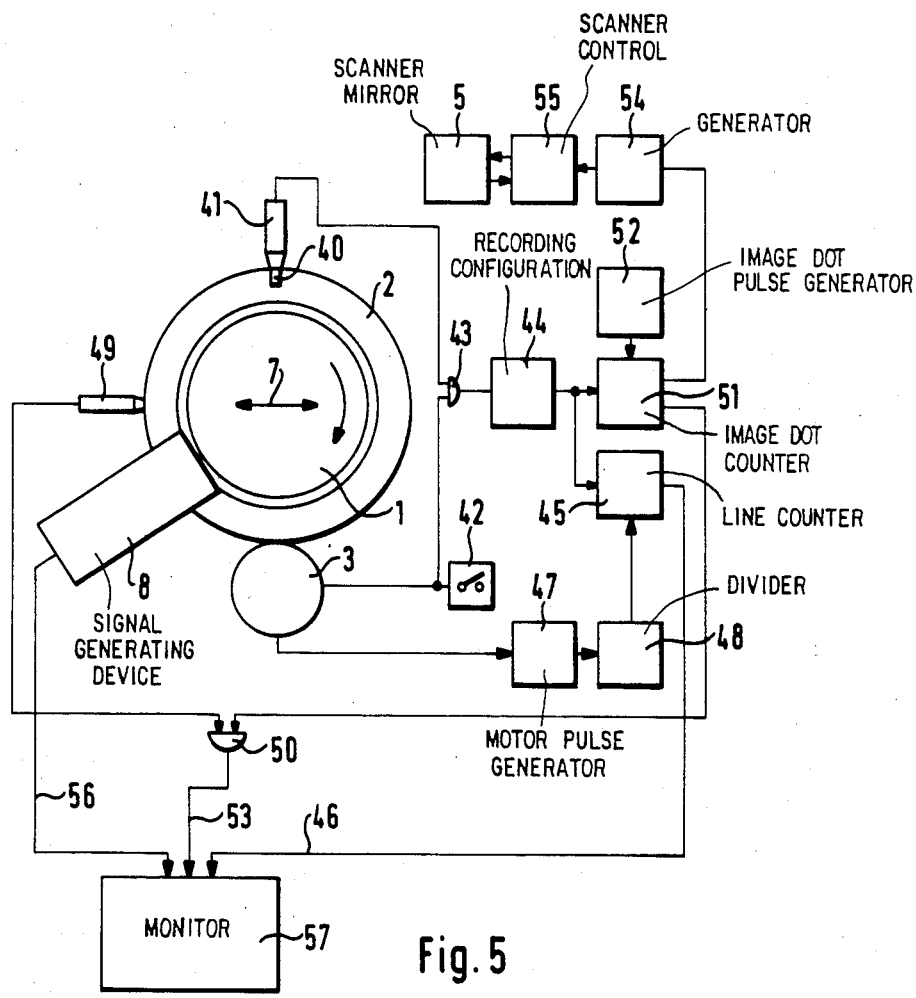
FIG. 5 shows, by way of example, a configuration for generation of evaluation signals.

In the variant in FIG. 5, a horizontal projection of the lens (1) to be analyzed is shown, which is turned in the direction of the arrow, scanning with the laser light beam (7) being in diametrical direction. The light section thus created is scanned by a signal generating device (8) such as is illustrated in FIG. 1. In order to preserve clarity, only one signal generating device of this type for signal acquisition has been illustrated here.

The rotary plate (2), in which the lens (1) is centered, is provided with a marking (40), which is detected by a receiver (41). The signal from the receiver (41) denotes the beginning of the image and, after actuation of the switch (42) for switching on the torque motor (3), is led via an AND circuit to a recording configuration (44), which initiates recording. The signals pass from the recording configuration (44) to a line-counter (45), adjacent to the output line (46) of which is the line pulse. The line-counter (45) is controlled via a motor pulse generator (47) and a divider (48).

A further receiver (49) acts together with the rotary plate (2), generating at the beginning of each line a signal which is fed to an AND circuit (50). A further signal is fed to this AND circuit via an image dot-counter (51), controlled by the image-dot pulse generator (52). An image-dot pulse signal is then adjacent to the output line of the AND circuit (50).

The image dot-counter (51) controls a generator (54) for the scanner function, i.e. for movement of the scanner mirror (5). The scanner control (55), which moves the scanner (5), is actuated via the generator (54).

The video signal is adjacent to the output (56) of the signal generating device (8). The signals via the lines (46, 53, 56) are fed to a receiver (57), which displays a monitor image of the selected surface of the lens (1). The surface flaws of the lens (1) are displayed brightly in this monitor image, whilst the flawless areas remain dark.

Instead of graphic evaluation via the monitor (57), a configuration can also be provided for electronic image evaluation such as described and illustrated in the Patent Application No. P 3620146.4/U.S. application Ser. No. 062,181, supra.

In summary, the present device is for testing components of transparent material for surface irregularities and occlusions. The component is scanned by means of a moving light ray in such a way that a light section of the component is produced. This light section is scanned by means of a device which is arranged at an inclined angle to the direction of impingement of the illumination ray. This device includes an image-forming optical system, in the focal plane of which an interchangeable mask is arranged for masking out the image of a plane of the test piece. The light rays which pass this mask, are admitted by a receiver, post-installed to which is a configuration for evaluation of the receiver signals.

By means of such a device, surface flaws in the component to be tested can be detected, the front and back of such component being, namely, separately detected.

In order to also be able to detect anisotropicly diffused surface flaws, for instance, smears, a third receiving system is provided, which is designed as an integral lens. This consists of several receivers arranged in a hemispherical shell, which covers the component to be tested.

We claim

1. A device for testing components of transparent material for surface irregularities and occlusions, comprising:
    means for rotatably mounting the component so that the component may be rotated on its axis;
    means for generating a light ray which moves linearly so that the light ray can dot-scan the component along a diameter of the component;
    at least one signal generating device disposed at a predetermined angle to the direction of impingement of the light ray for detecting light diffracted by the surface irregularities and occlusions of the component and then generating a signal representative of the irregularity or occlusion, said signal generating device comprising:
        an image forming optical system;
        an interchangeable mask disposed at the focal plane of said image forming optical system for selecting the image of a plane of the component; and
        a receiver for receiving the light rays passing said mask and generating a signal representative of the light rays received; and
    a signal evaluation device for evaluating the signals produced in said signal generating device.

2. A device as defined in claim 1, wherein said signal generating device further comprises:
    a beam splitter disposed between said image forming system and said mask so that said beam splitter redirects a portion of the light to an additional focal plane;
    an additional interchangeable mask disposed at said additional focal plane; and
    an additional receiver for receiving the light rays passing said additional mask and generating a signal representative of the light rays received.

3. A device as defined in claim 1, wherein said image forming system comprises a zoom lens.

4. A device as defined in claim 1, further comprises two of said signal generating devices symmetrically disposed to the rotational axis of the component.

5. A device as defined in claim 1, further comprising:
    a hemispherical shell disposed above the component; and
    additional light detecting means arranged around said hemispherical shell.

6. A device as defined in claim 5, wherein said additional light detecting means generates signals which are electrically linked.

7. A device as defined in claim 5, wherein said additional light detecting means comprises:

several lenses disposed in openings in said hemispherical shell;
a common receiver; and
a respective flexible optical fiber connected between each respective lens and said common receiver for transmitting the light received by each of said lenses to said common receiver.

* * * * *